US00PP12936P2

(12) United States Plant Patent
Zaiger et al.

(10) Patent No.: US PP12,936 P2
(45) Date of Patent: Sep. 10, 2002

(54) INTERSPECIFIC TREE NAMED 'FLAVOR TREAT'

(76) Inventors: Chris Floyd Zaiger, 929 Grimes Ave.; Leith Marie Gardner, 1207 California Ave.; Gary Neil Zaiger, 1907 Grimes Ave.; Grant Gene Zaiger, 4005 California Ave., all of Modesto, CA (US) 95358

( * ) Notice: Subject to any disclaimer, the term of this patent is extended or adjusted under 35 U.S.C. 154(b) by 38 days.

(21) Appl. No.: 09/816,194

(22) Filed: Mar. 26, 2001

(51) Int. Cl.[7] ..... A01H 5/00
(52) U.S. Cl. ..... Plt./180
(58) Field of Search ..... Plt./180

*Primary Examiner*—Bruce R. Campell
*Assistant Examiner*—Anne Marie Grünberg

(57) ABSTRACT

A new and distinct variety of interspecific tree. The following features of the tree and its fruit are characterized with the tree budded on Citation Rootstock (U.S. Plant Pat. No. 5,112), grown on Handford sandy loam soil with Storie Index rating 95, in USDA Hardiness Zone 9, near Modesto, Calif., with standard commercial fruit growing practices, such as, pruning, thinning, spraying, irrigation and fertilization. Its novelty consist of the following combination of desirable features:

1. Fruit with very good flavor and eating quality.
2. Heavy and regular production of fruit.
3. Fruit with an attractive garnet red skin color.
4. Relatively uniform size fruit throughout the tree.
5. Fruit with firm flesh, good handling and shipping quality.
6. Fruit holding firm on the tree 10 to 14 days after shipping ripe.
7. Fruit ripening in the late maturity season.

1 Drawing Sheet

BACKGROUND OF THE VARIETY

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of plums, apricot, and interspecifics which are known to us, and mentioned herein are, Mariposa Plum (U.S. Plant Pat. No. 111), Red Beaut Plum (U.S. Plant Pat. No. 2,539), Flaming Gold Apricot (U.S. Plant Pat. No. 2,822), Flavor Supreme Interspecific (U.S. Plant Pat. No. 6,763), Citation Interspecific (U.S. Plant Pat. No. 5,112) and Flavor Gem Interspecific (U.S. Plant Pat. No. 10,915).

ORIGIN OF THE VARIETY

The new and distinct interspecific tree consists of the combination of *Prunus persica, Prunus armeniaca,* and *Prunus salicina.* It was developed by us in our experimental orchard located near Modesto, Calif., as a first generation cross between two seedlings with field identification numbers 82EG355 and 324LF168. (These non-patented seedlings were developed and selected by us for future parents in our ongoing breeding program). The maternal parent (82EG355) originated from the crossing of two seedlings. The first seedling originated by crossing Mariposa Plum (U.S. Plant Pat. No. 111) with a plumcot, then selecting a seedling from this cross and crossing it with another plumcot, both plumcot selections originated from crossing Red Beaut Plum (U.S. Plant Pat. No. 2,539) with an apricot of unknown parentage. The second seedling originated from crossing a plum of unknown parentage with a plumcot having parentage of Red Beaut Plum (U.S. Plant Pat. No. 2,539) crossed with an apricot of unknown parentage; a seedling was selected from this parentage and crossed with a seedling peach cot, which was selected from a cross of Flaming Gold Apricot (U.S. Plant Pat. No. 2,822) with a peach of unknown parentage.

The paternal parent 324LF168 originated from a cross of two seedlings. The first seedling originated from an apricot of unknown parentage crossed with a plumcot seedling with the parentage of Red Beaut Plum (U.S. Plant Pat. No. 2,539) crossed with an apricot of unknown parentage. The second seedling originated as an open pollinated seedling from Flavor Supreme Interspecific (U.S. Plant Pat. No. 6,763).

We planted and maintained a large group of these interspecific crosses on their own root system. In September of 1995, we removed a bud stick from the most vigorous seedlings and budded these to Citation Rootstock (U.S. Plant Pat. No. 5,112). It was from these budded trees that we recognized the outstanding fruit characteristics of the present variety and selected it for commercialization.

ASEXUAL REPRODUCTION OF THE VARIETY

Asexual reproduction of the new and distinct variety of interspecific tree was by budding to Citation Rootstock, (U.S. Plant Pat. No. 5,112) a standard rootstock for plums and interspecifics in California, as performed by us in our experimental orchard located near Modesto, Calif., and shows that reproductions run true to the original tree and all characteristics of the tree and its fruit are established and transmitted through succeeding asexual propagations.

SUMMARY OF THE VARIETY

The present new and distinct interspecific tree consists of the following crosses for the maternal parent [(Plum×

Plumcot)×(Plumcot)×(Plum×Plumcot)×Peach Cot)] and the paternal crosses are [(Cot×Plumcot)×Interspecific Flavor Supreme]. The new tree is of large size, vigorous, upright growth and a productive and regular bearer of large, firm, clingstone fruit, maturing in the late maturity season. The fruit is further characterized by being relatively uniform in size throughout the tree, having firm flesh with good storage and shipping quality, having a good balance between acid and sugar. The flavor and eating quality being very good with an average Brix of 19.6°. In comparison to the fruit of the late maturing Flavor Gem Interspecific (U.S. Plant Pat. No. 10,915), the fruit is more round in shape, is clingstone instead of freestone, and is approximately 3 weeks later in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to shown flesh color, pit cavity and the stone remaining in place. The photographic illustration was taken shortly after being picked (shipping ripe) and the colors are as true as is reasonably possible in a color representation of this type.

DESCRIPTION OF THE VARIETY

The following is a detailed botanical description of the new variety of interspecific tree, its flowers, foliage and fruit, as based on observations of 5 year old specimens budded on Citation Rootstock (U.S. Plant Pat. No. 5,112) and grown near Modesto, Calif., with color terminology (except those in common terms) in accordance with Reinhold Color Atlas by A. Kornerup and J. H. Wanscher.

Tree:

*Size.*—Large. Pruned 10 to 12 feet in height and width for economical harvesting of fruit.

*Vigor.*—Vigorous. New growth of 5 to 6 feet in height the first growing season. Varies with type of soil, fertility and cultural practices.

*Growth.*—Upright. Crotch angle approximately 30°. As tree matures, heavy production tends to spread width of tree.

*Branching habit.*—Upright. Spreading of tree and crotch angle increases with weight of fruit.

*Productivity.*—Productive. Sets 1½ to several times the amount of fruit desired for marketable size fruit. Varies with climatic conditions during bloom time, thinning and spacing of fruit is necessary.

*Bearer.*—Has set heavy crop for 4 consecutive years. No alternate bearing observed.

*Fertility.*—Self-sterile, pollenizer necessary.

*Density.*—Medium dense. Usually pruned to vase shape to increase the amount of sunlight to center of tree, improve fruit color, brix and health of fruitwood.

*Hardiness.*—Tree grown in USDA Hardiness Zone 9. Winter chilling requirement is approximately 750 hours at or below 45° F. Hardy for all stone fruit growing areas of California.

Trunk:

*Size.*—Large. Average circumference of 16 inches when measured at a height of 12 inches above ground on 5 year old trees.

*Stocky.*—Medium stocky.

*Surface.*—Medium shaggy, increases with age of tree.

*Color.*—Varies from brown to tobacco brown (5-D-3) to (5-F-6).

Branches:

*Size.*—Medium. Average circumference 8 inches, when measured at a height of 38 inches above ground. Crotch angle — approximately 30°.

*Surface texture.*—Varies from smooth on new growth to medium rough on older growth; roughness increases with age of branches.

*Lenticels.*—Medium size. Average length 3/32 inch. Average width 1/32 inch. Size increases as branch grows larger. Average number of 42 in a 4 square inch surface. Color varies from Pompeian yellow to brownish yellow (5-C-6) to (5-C-7).

*Color.*—First years growth exposed to sunlight brownish orange (6-C-5), in shaded areas grayish green (1-D-6). Mature growth light brown to brown (5-D-7) to (5-E-5), varies with age of growth.

Leaves:

*Size.*—Medium. Average length 3 37/64 inches. Average width 1 43/64 inches.

*Form.*—Oblanceolate.

*Margin.*—Serrulate.

*Thickness.*—Thin to medium.

*Surface texture.*—Upper surface relatively smooth, slightly indented over leaf veins. Glabrous. Lower surface relatively smooth, small ridges created by midrib and pinnate venation. Glabrous.

*Petiole.*—Average length — 27/64 inch. Average width — 1/16 inch. Color — light green to light yellow green (30-B-6) to (30-C-6).

*Glands.*—Globose. Number varies from 0 to 2, average number 1. Size — small, average length 1/32 inch. Color — reddish brown (9-D-7). Location — on upper portion of petiole and base of leaf blade.

*Color.*—Upper surface — green to dark green (29-F-6) to (29-F-7). Lower surface — grayish green to dull green (29-E-4) to (29-E-5).

*Apex.*—Acuminate.

*Base.*—Cuneate.

Flower buds:

*Size.*—Small to medium. Average length — 19/64 inch. Average width — 11/64 inch. Four days before opening.

*Hardiness.*—Hardy with respect to California winters.

*Form.*—Plump, conical, becomes more elongated as bud matures.

*Color.*—White (2-A-1).

*Number of buds per spur.*—Varies from 4 to 14. Average number 7.

Flowers:

*Size.*—Medium. Average height 29/64 inch. Average width 47/64 inch.

*Petal.*—Shape — elliptical, narrows at point of attachment. Usually 5 per flower, alternately arranged to sepals. Average length — 25/64 inch. Average width — 9/32 inch. Color — white (1-A-1). Surface of outer edge varies from smooth to slightly scalloped. Color — white (2-A-1).

*Sepals.*—Size — medium, alternately arranged to petals. Number — 5. Average length — 7/64 inch. Average width of base 5/64 inch. Color varies from light yellowish green on upper surface (29-A-8), to yellowish green (29-B-8) on lower surface. Both surfaces glabrous.

*Stamens*.—Number varies from 34 to 40 per flower. Average number 37. Average length 3/8 inch. Filament color — white (1-A-1). Anther color — dark yellow (4-A-8).

*Pollen*.—Present, pollen sacs large and full. Color — pale yellow to light yellow (3-A-3) to (3-A-5).

*Pollenizer*.—Self-sterile, needs pollenizer.

*Pistil*.—Normally one. Average length 21/64 inch. Color — yellowish white (2-A-2). Stigma positioned approximately 1/16 inch below anthers. Surface — glabrous.

*Fragrance*.—Slight.

*Blooming period*.—Date of First Bloom Feb. 27, 2000. Date of Petal Fall Mar. 9, 2000. Varies slightly with climatic conditions.

*Color*.—White (2-A-1).

*Number of flowers per bud*.—Varies from 1 to 3. Average number — 2.

*Pedicel*.—Color — olive green (2-E-7). Average length — 15/64 inch. Average width — 3/32 inch.

Fruit:

*Maturity when described*.—Firm ripe.

*Date of first picking*.—Sep. 6, 2000.

*Date of last picking*.—Sep. 11, 2000. Varies slightly with climatic conditions.

*Size*.—Large. Relatively uniform throughout the tree. Average diameter axially 2½ to 2¾ inches. Average transversely in suture plane 2¾ to 2⅞ inches. Average weight 210 grams. Average weight varies slightly with fertility of the soil, amount of thinning and climatic conditions.

*Form*.—Globose. Relatively uniform.

*Suture*.—Shallow, extends from base to apex.

*Ventral surface*.—Nearly smooth, very slightly lipped.

*Apex*.—Nearly rounded, varies from slightly retuse to rounded.

*Base*.—Retuse.

*Cavity*.—Rounded to slightly elongated in suture plane. Average depth — 3/8 inch. Average breadth — 5/8 inch.

Stem:

*Size*.—Average length 5/8 inch. Average diameter 1/8 inch, enlarged at point of fruit attachment.

*Color*.—Light green to linden green (2-C-4) to (2-C-5).

Flesh:

*Ripens*.—Evenly.

*Texture*.—Firm, meaty.

*Fibers*.—Few, small, tender.

*Firmness*.—Firm, having good handling and shipping quality.

*Aroma*.—Slight.

*Amydgalin*.—None.

*Eating quality*.—Very good.

*Flavor*.—Very good, sweet, mild, good balance between acid and sugar.

*Juice*.—Juicy, enhances flavor and eating quality.

*Brix*.—Average Brix 19.6°. Varies slightly with amount of fruit per tree and climatic conditions.

*Color*.—Light yellow to yellow (4-A-4) to (4-A-6). Pit cavity — grayish orange to brownish orange (5-C-6) to (5-D-6).

Skin:

*Color*.—Butter yellow to maize yellow (4-A-5) to (4-A-6) ground color. Overspread with garnet red to dark maroon (11-E-8) to (11-F-8). Very small, randomly spaced areas of ground color showing, giving a speckling pattern.

*Thickness*.—Medium, tenacious to the flesh.

*Texture*.—Smooth, not associated with acidity or bitterness.

*Bloom*.—Moderate.

*Tendency to crack*.—None.

*Astringency*.—Lacking.

Stone:

*Type*.—Clingstone.

*Size*.—Small. Average length 7/8 inch. Average width 5/8 inch. Average thickness 3/8 inch.

*Form*.—Obovoid.

*Base*.—Straight.

*Apex*.—Acuminate. Length — short, small, approximately 3/32 inch in length.

*Sides*.—Equal.

*Surface*.—Irregularly pitted throughout with very small pits, randomly spaced. One long groove running from base to apex on each side of suture. One long, low, narrow ridge from base to apex, usually on one side of stone, a few stones have one on both sides. Very small, short ridges running from base toward apex, approximately ¼ distance of stone.

*Tendency to split*.—None.

*Color*.—Light brown to dark blond (5-C-4) to (5-D-4) when dry.

Use: Dessert. Market — local and long distance.

Keeping quality: Good, held firm in cold storage (38–42° F.) for two weeks without internal breakdown or loss of flavor or eating quality.

Shipping quality: In picking and packing trials minimal bruising of flesh or skin scarring was observed.

Disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during normal indexing or plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of interspecific tree, substantially as illustrated and described, characterized by its large size, vigorous upright growth and being a productive and regular bearer of large, clingstone fruit with very good flavor and eating quality; the fruit is further characterized by having firm flesh with good storage and shipping quality and in comparison to the fruit of the Flavor Gem Interspecific (U.S. Plant Pat. No. 10,915), the fruit of the new variety is larger in size, clingstone instead of freestone and is approximately three weeks later in maturity.

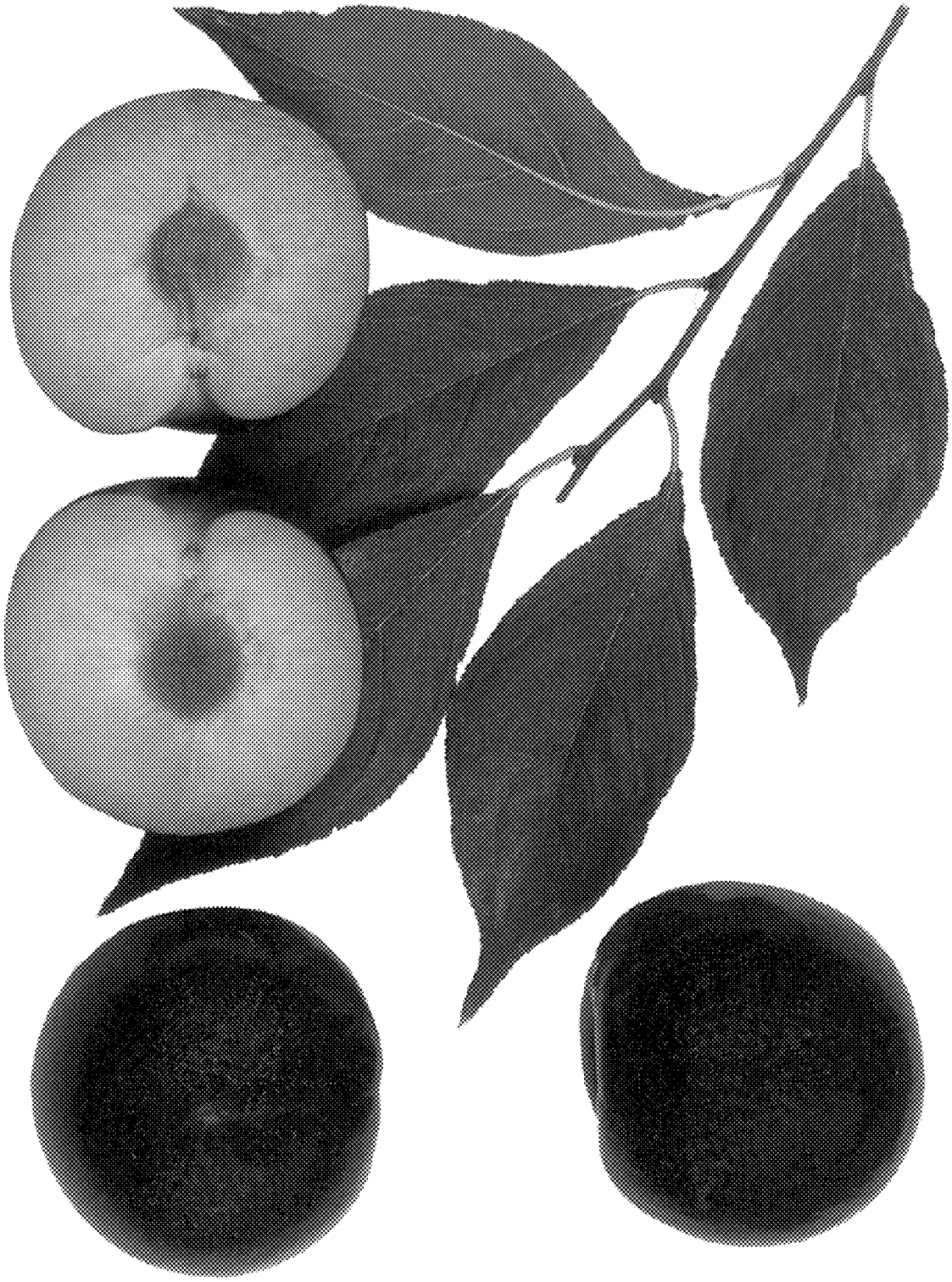

* * * * *